United States Patent
Nomura et al.

(10) Patent No.: US 7,851,617 B2
(45) Date of Patent: Dec. 14, 2010

(54) INDOLE DERIVATIVES

(75) Inventors: Sumihiro Nomura, Osaka (JP); Shigeki Sakamaki, Osaka (JP)

(73) Assignee: Mitsubishi Tanabe Pharma Corporation, Osaka-shi (JP)

(*) Notice: Subject to any disclaimer, the term of this patent is extended or adjusted under 35 U.S.C. 154(b) by 638 days.

(21) Appl. No.: 11/878,760

(22) Filed: Jul. 26, 2007

(65) Prior Publication Data

US 2008/0027122 A1  Jan. 31, 2008

Related U.S. Application Data

(60) Provisional application No. 60/820,604, filed on Jul. 27, 2006, provisional application No. 60/886,178, filed on Jan. 23, 2007.

(51) Int. Cl.
C07H 19/044 (2006.01)
C07H 19/056 (2006.01)
A01N 43/04 (2006.01)
A61K 31/70 (2006.01)

(52) U.S. Cl. ........................ 536/28.6; 514/43
(58) Field of Classification Search .............. None
See application file for complete search history.

(56) References Cited

U.S. PATENT DOCUMENTS

| | | | |
|---|---|---|---|
| 5,424,406 A | 6/1995 | Tsujihara et al. |
| 5,731,292 A | 3/1998 | Tsujihara et al. |
| 5,830,873 A | 11/1998 | Tsujihara et al. |
| 6,414,126 B1 | 7/2002 | Ellsworth et al. |
| 6,515,117 B2 | 2/2003 | Ellsworth et al. |
| 6,562,791 B1 | 5/2003 | Maurya et al. |
| 2001/0041674 A1 | 11/2001 | Tomiyama et al. |
| 2002/0052326 A1 | 5/2002 | Washburn |
| 2002/0111315 A1 | 8/2002 | Washburn et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0293251 A1 | 12/2006 | Urbanski et al. |
| 2007/0060545 A1 | 3/2007 | Nomura et al. |
| 2008/0119422 A1 * | 5/2008 | Nomura et al. ............... 514/43 |

FOREIGN PATENT DOCUMENTS

| | | |
|---|---|---|
| CA | 2494177 A1 | 2/2004 |
| CL | 203-06 | 5/2006 |
| EP | 1528066 A1 | 5/2005 |
| EP | 1 803 729 A1 | 7/2007 |
| JP | 2001-288178 A | 10/2001 |
| JP | 2003-12686 A | 1/2003 |
| WO | WO-01/27128 A1 | 4/2001 |
| WO | WO-01/68660 A1 | 9/2001 |
| WO | WO-01/74834 A1 | 10/2001 |
| WO | WO-01/74835 A1 | 10/2001 |
| WO | WO-02/053573 A1 | 7/2002 |
| WO | WO-02/068439 A1 | 9/2002 |
| WO | WO-02/068440 A1 | 9/2002 |
| WO | WO-02/083066 A2 | 10/2002 |
| WO | WO-02/088157 A1 | 11/2002 |
| WO | WO-03/011880 A1 | 2/2003 |
| WO | WO-03/020737 A1 | 3/2003 |
| WO | WO-03/099836 A1 | 12/2003 |
| WO | WO-2004/007517 A1 | 1/2004 |
| WO | WO-2004/013118 A1 | 2/2004 |
| WO | WO-2004/014931 A1 | 2/2004 |
| WO | WO-2004/019958 A1 | 3/2004 |
| WO | WO-2004/052902 A1 | 6/2004 |
| WO | WO-2004/052903 A1 | 6/2004 |
| WO | WO-2004/080990 A1 | 9/2004 |
| WO | WO-2005/012326 A1 | 2/2005 |

(Continued)

OTHER PUBLICATIONS

R.H.Unger et al., Diabetologia, vol. 28, (1985), pp. 119-121.

(Continued)

*Primary Examiner*—Shaojia Anna Jiang
*Assistant Examiner*—Layla Bland
(74) *Attorney, Agent, or Firm*—Birch, Stewart, Kolasch & Birch, LLP

(57) ABSTRACT

Novel indole derivatives of formula (I) or a pharmaceutically acceptable salt thereof:

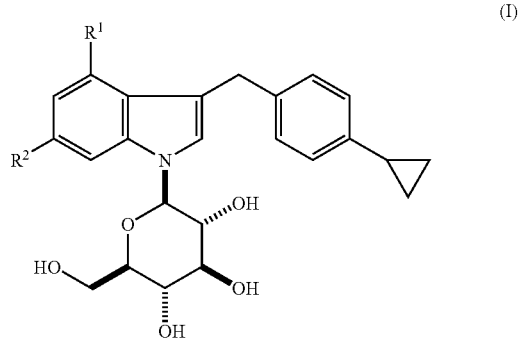

wherein $R^1$ is fluorine, or chlorine, and $R^2$ is hydrogen, or fluorine, which are SGLT inhibitors and are useful for treatment or prevention of diabetes and related conditions.

12 Claims, No Drawings

FOREIGN PATENT DOCUMENTS

WO    WO-2006/035796 A1    4/2006

OTHER PUBLICATIONS

Luciano Rossetti M.D. et al., *Diabetes Care*, vol. 13, No. 6, (Jun. 1990), pp. 610-630.

Luciano Rossetti et al., *J. Clin. Invest.*, vol. 79, (May 1987), pp. 1510-1515.

Luciano Rossetti et al., *J. Clin. Invest..*, vol. 80, (Oct. 1987), pp. 1037-1044.

Barbara B. Kahn et al., *J. Clin Invest.*, vol. 87, (Feb. 1991), pp. 561-570.

Kenji Tsujihara et al., *J. Med. Chem.*, vol. 42, (1999), pp. 5311-5324.

Kenji Arakawa et al., *British Journal of Pharmacology*, vol. 132, (2001), pp. 578-586.

Ahmad et al., *Nucleosides, Nucleotides & Nucleic Acids*, vol. 20, No. 9, (2001), pp. 1671-1682.

Zamani et al., *Journal of the Chinese Chemical Society*, vol. 49, (2002), pp. 1041-1044.

Maatooq et al., *Phytochemistry*, vol. 44, No. 1, (Jan. 1997), pp. 187-190.

Hongu et al., Chem. Pharm. Bull., vol. 46, No. 1, pp. 22-33, (1998).

\* cited by examiner

INDOLE DERIVATIVES

This Nonprovisional application claims priority under 35 U.S.C. §119(e) on U.S. Provisional Application No(s). 60/820,604 and 60/886,178 filed on Jul. 27, 2006 and Jan. 23, 2007; respectively, the entire contents of which are hereby incorporated by reference.

TECHNICAL FIELD

The present invention relates to novel indole derivatives possessing activity as inhibitors of sodium-dependent glucose transporters (SGLT) found in the intestine or kidney.

BACKGROUND ART

Diet therapy and exercise therapy are essential in the treatment of diabetes mellitus. When these therapies do not sufficiently control conditions of patients, insulin or anti-diabetic agents are used. Examples of the anti-diabetic agents include, at the present, biguanides, sulfonylureas, insulin-sensitizing agents and α-glucosidase inhibitors. However, these anti-diabetic agents have various side effects. For example, biguanides cause lactic acidosis, sulfonylureas cause significant hypoglycemia, insulin-sensitizing agents cause edema and heart failure, and α-glucosidase inhibitors cause abdominal bloating and diarrhea. Under these circumstances, new anti-diabetic drugs that eliminate these side effects are desired.

Recently, it has been reported that hyperglycemia participates in the onset and progression of diabetes mellitus. This theory is called glucose toxicity theory. Namely, chronic hyperglycemia leads to decrease of insulin secretion and insulin sensitivity, the plasma glucose level is elevated, and as a result, diabetes mellitus is self-exacerbated [cf., Diabetologia, vol. 28, p. 119 (1985); Diabetes Care, vol. 13, p. 610 (1990), etc.]. Based on this theory, it is expected that normalization of plasma glucose level interrupts the aforementioned self-exacerbating cycle and the prevention or treatment of diabetes mellitus can be achieved.

It is considered that one method for the treatment of hyperglycemia is to excrete an excess amount of glucose directly into urine so that the blood glucose concentration can be normalized. For example, by inhibiting sodium-dependent glucose transporters being present at the proximal convoluted tubule of kidney, the re-absorption of glucose at the kidney is inhibited whereby the excretion of glucose into urine can be promoted and the blood glucose level can be decreased. In fact, it is confirmed that by continuous subcutaneous administration of an SGLT inhibitor, phlorizin, to diabetic animal models, the blood glucose level thereof can be normalized, and that by keeping the blood glucose level normal for a long time, the insulin secretion and insulin resistance can be improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with an SGLT inhibitor for a long time, insulin secretion response and insulin sensitivity of the animal models are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), etc.].

In view of the above, SGLT inhibitors are expected to improve insulin secretion and insulin resistance by decreasing the blood glucose level in diabetic patients and to prevent the onset and progress of diabetes mellitus and diabetic complications.

WO 2006/035796 discloses N-β-D-glycopyranosyl nitrogen-containing heterobicyclic compounds of the following formula:

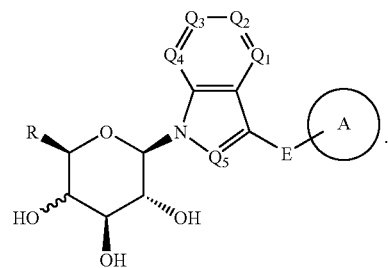

The above compounds are described as SGLT1 and/or SGLT2 inhibitors and are useful for the prevention or treatment of diabetes and related diseases.

DISCLOSURE OF INVENTION

The present invention relates to novel indole derivatives of formula, (I), or a pharmaceutically acceptable salt thereof:

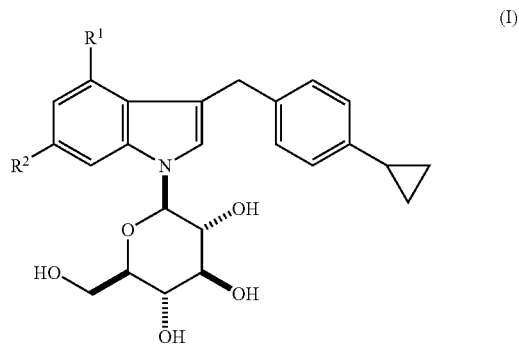

wherein $R^1$ is fluorine, or chlorine, and $R^2$ is hydrogen, or fluorine.

The compounds of formula (I) possess activity as inhibitors of SGLT found in the intestine and kidney of mammals, and are useful in the treatment or prevention of diabetes mellitus and diabetic complications such as diabetic retinopathy, diabetic neuropathy, diabetic nephropathy, and delayed wound healing, and related diseases.

The pharmaceutically acceptable salts of the compounds of formula (I) include, for example, a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

In addition, pharmaceutically acceptable salts of the compounds of formula (I) include an intramolecular salt, hydrate, solvate or polymorphism thereof.

In a preferable embodiment of the present invention, $R^2$ is hydrogen.

As the indole moiety, 4-fluoroindole (i.e., $R^1$ is fluorine and $R^2$ is hydrogen), 4-chloroindole (i.e., $R^1$ is chlorine and $R^2$ is hydrogen), or 4,6-difluoroindole (i.e., $R^1$ and $R^2$ are both fluorine) is preferable.

A preferable compound of the present invention is selected from the following group:
4-chloro-3-(4-cyclopropylphenylmethyl)-1-(β-D-gluco-pyranosyl) indole,
3-(4-cyclopropylphenylmethyl)-4-fluoro-1-(β-D-gluco-pyranosyl) indole,
4-chloro-3-(4-cyclopropylphenylmethyl)-6-fluoro-1-(β-D-gluco-pyranosyl) indole, and
3-(4-cyclopropylphenylmethyl)-4,6-difluoro-1-(β-D-gluco-pyranosyl) indole;

or a pharmaceutically acceptable salt thereof.

The characteristic of the present compounds is the combination of a p-cyclopropylphenylmethyl group at the 3-position of the indole ring and a halogen atom (particularly fluorine or chlorine) at the 4-position.

The compounds of the present invention possess activity as inhibitors of sodium-dependent glucose transporters, and show excellent blood glucose lowering effect.

The compounds of the present invention also demonstrate favorable characteristics in side effects and/or commercial viability.

The compounds of the present invention are expected to be useful in the treatment, prevention or delaying the progression or onset of diabetes mellitus (type 1 and type 2 diabetes mellitus, etc.), diabetic complications (such as diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hyper-tension.

The compounds of the present invention or a pharmaceutically acceptable salt thereof may be administered either orally or parenterally, and can be used in the form of a suitable pharmaceutical preparation. Suitable pharmaceutical preparations for oral administration include, for example, solid preparations such as tablets, granules, capsules, and powders, or solution preparations, suspension preparations, emulsion preparations, and the like. Suitable pharmaceutical preparations for parenteral administration include, for example, suppositories; injection preparations or intravenous drip preparations, using distilled water for injection, physiological saline solution or aqueous glucose solution; and inhalant preparations.

The pharmaceutical compositions herein will contain, per dosage unit, e.g., tablet, capsule, powder, injection, suppository, teaspoonful and the like, from about 0.01 mg/kg to about 100 mg/kg body weight (preferably from about 0.01 mg/kg to about 50 mg/kg; and, more preferably, from about 0.01 mg/kg to about 30 mg/kg) of the active ingredient, and may be given at a dosage of from about 0.01 mg/kg/day to about 100 mg/kg/day (preferably from about 0.01 mg/kg/day to about 50 mg/kg/day and more preferably from about 0.01 mg/kg/day to about 30 mg/kg/day). The method of treating a disorder described in the present invention may also be carried out using a pharmaceutical composition comprising any of the compounds as defined herein and a pharmaceutical acceptable carrier. The dosage form will contain from about 0.01 mg/kg to about 100 mg/kg (preferably from about 0.01 mg/kg to about 50 mg/kg; and, more preferably, from about 0.01 mg/kg to about 30 mg/kg) of the active ingredient, and may be constituted into any form suitable for the mode of administration selected. The dosages, however, may be varied depending upon administration routes, the requirement of the subjects, the severity of the condition being treated and the compound being employed. The use of either daily administration or post-periodic dosing may be employed.

The compounds of formula (I) may be used, if necessary, in combination with one or more of other anti-diabetic agents, antihyperglycemic agents and/or agents for treatment of other diseases. The present compounds and these other agents may be administered in the same dosage form, or in a separate oral dosage form or by injection.

Examples of the other anti-diabetic agents and anti-hyper glycemic agents include insulin, insulin secretagogues, insulin sensitizers, or other antidiabetic agents having an action mechanism different from SGLT inhibition. Specifically, examples of these agents are biguanides, sulfonylureas, α-glucosidase inhibitors, PPARγ agonists (e.g., thiazolidinedione compounds), PPARα/γ dual agonists, PPARpan agonists, dipeptidyl peptidase IV (DPP4) inhibitors, mitiglinide, nateglinide, repaglinide, insulin, glucagon-like peptide-1 (GLP-1) and its receptor agonists, PTP1B inhibitors, glycogen phosphorylase inhibitors, RXR modulators, glucose 6-phosphatase inhibitors, GPR40 agonists/antagonists, GPR119 agonists, GPR120 agonists, glucokinase (GK) activators, and fructose 1,6-bisphosphatase (FBPase) inhibitors.

Examples of the agents for treatment of other diseases include anti-obesity agents, antihypertensive agents, anti-platelet agents, anti-atherosclerotic agents and hypolipidemic agents.

The anti-obesity agents which may be optionally employed in combination with the compound of the present invention include $\beta_3$ adrenergic agonists, lipase inhibitors, serotonin (and dopamine) reuptake inhibitors, thyroid hormone receptor beta drugs, anorectic agents, NPY antagonists, Leptin analogs, MC4 agonists and CB1 antagonists.

The anti-platelet agents which may be optionally employed in combination with the compound of the present invention include abciximab, ticlopidine, eptifibatide, dipyridamole, aspirin, anagrelide, tirofiban and clopidogrel.

The anti-hypertensive agents which may be optionally employed in combination with the compound of the present invention include ACE inhibitors, calcium antagonists, alpha-blockers, diuretics, centrally acting agents, angiotensin-II antagonists, beta-blockers, renin inhibitors and vasopeptidase inhibitors.

The hypolipidemic agents which may be optionally employed in combination with the compound of the present invention include MTP inhibitors, HMG CoA reductase inhibitors, squalene synthetase inhibitors, squalene epoxidase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, nicotinic acid and derivatives thereof, CETP inhibitors, and ABC A1 upregulators.

The compounds of formula (I) may be used in combination with agents for treatment of diabetic complications, if necessary. These agents include, for example, PKC inhibitors, aldose reductase inhibitors, and/or ACE inhibitors.

The various agents described above may be employed in the same dosage form with compounds of formula (I) or in different dosage forms, in dosages and regimens as generally known in the art.

The dosage of those agents may vary according to, for example, ages, body weight, conditions of patients, administration routes, and dosage forms.

These pharmaceutical compositions may be orally administered to mammalian species including human beings, apes, and dogs, in the dosage form of, for example, tablet, capsule, granule or powder, or parenterally administered in the form of injection preparation, or intranasally, or in the form of transdermal patch.

The compounds of formula (I) of the present invention or a pharmaceutically acceptable salt thereof, can be prepared by deprotecting compounds of formula (II):

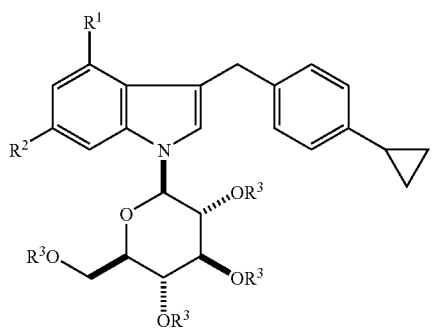

wherein $R^3$ is a protecting group for a hydroxy group, and the other symbols are the same as defined above, followed by converting the resulting compound into a pharmaceutically acceptable salt, if desired.

The compounds of formula (II) are believed to be novel and form a further aspect of this invention.

In the compounds of formula (II), the protecting group for a hydroxy group can be selected from conventional protecting groups for a hydroxy group, and examples of such protecting group include benzyl, alkanoyl such as acetyl, and alkylsilyl such as trimethylsilyl, triethylsilyl and t-butyldimethylsilyl. Further, the protecting group for a hydroxy group may form acetal or silylacetal together with adjacent hydroxy groups. Examples of such protecting group include an alkylidene group such as isopropylidene and sec-butylidene, a benzylidene group, and a dialkylsilylene group such as di-tert-butylsilylene group. Preferably, $R^3$ is alkanoyl such as acetyl.

The deprotection can be carried out according to kinds of the protecting group to be removed, and conventional methods such as reduction, hydrolysis, acid treatment, and fluoride treatment, can be used for the deprotection.

For example, when a benzyl group is to be removed, the deprotection can be carried out by (1) catalytic reduction using a palladium catalyst (e.g., palladium-carbon and palladium hydroxide) under hydrogen atmosphere in a suitable inert solvent (e.g., methanol, ethyl alcohol, and ethyl acetate); (2) treatment with an dealkylating agent such as boron tribromide, boron trichloride, boron trichloride•dimethylsulfide complex, or iodotrimethylsilane in an inert solvent (e.g., dichloromethane); or (3) treatment with an alkylthiol such as ethanethiol in the presence of a Lewis acid (e.g., boron trifluoride•diethyl ether complex) in a suitable inert solvent (e.g., dichloromethane).

When a protecting group is removed by hydrolysis, the hydrolysis can be carried out by treating the compounds of formula (II) with a base (e.g., sodium hydroxide, potassium hydroxide, lithium hydroxide, sodium methoxide, and sodium ethoxide) in a suitable inert solvent (e.g., tetrahydrofuran, dioxane, methanol, ethyl alcohol, and water).

Acid treatment can be carried out by treating the compounds of formula (II) with an acid (e.g., hydrochloric acid, p-toluene-sulfonic acid, methanesulfonic acid, and trifluoroacetic acid) in a suitable solvent (e.g., methanol, and ethyl alcohol).

In case of the fluoride treatment, it can be carried out by treating the compounds of formula (II) with a fluoride (e.g., hydrogen fluoride, hydrogen fluoride-pyridine, tetrabutylammonium fluoride, etc.) in a suitable inert solvent (e.g., acetic acid, alcohols (methanol, ethyl alcohol, etc.), acetonitrile, and tetrahydrofuran).

The deprotection reaction can be preferably carried out at lowered, ambient or elevated temperature, for example, from 0° C. to 50° C., more preferably from 0° C. to room temperature.

The compounds of the present invention thus obtained may be isolated and purified by a conventional method well known in the organic synthetic chemistry such as recrystallization, column chromatography, thin layer chromatography, and the like.

The compounds of formula (II) can be prepared in accordance with steps described in Scheme 1 or Scheme 2.

During any of the processes for preparation of the compounds of the present invention, it may be necessary and/or desirable to protect sensitive or reactive groups on any of the molecules concerned. This may be achieved by means of conventional protecting groups. For a general description of protecting groups and their use, see T. W. Greene et al., "Protecting Groups in Organic Synthesis", John Wiley & Sons, New York, 1999. The protecting groups may be removed at a subsequent step using methods known to those skilled in the art.

Scheme 1:

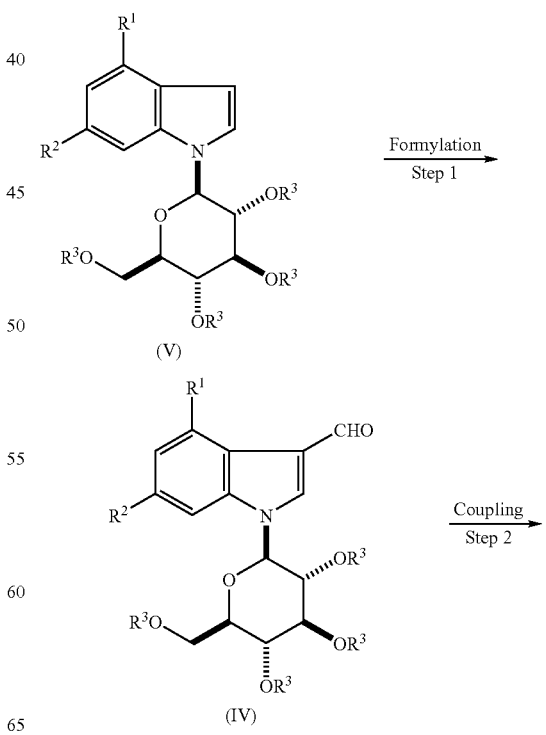

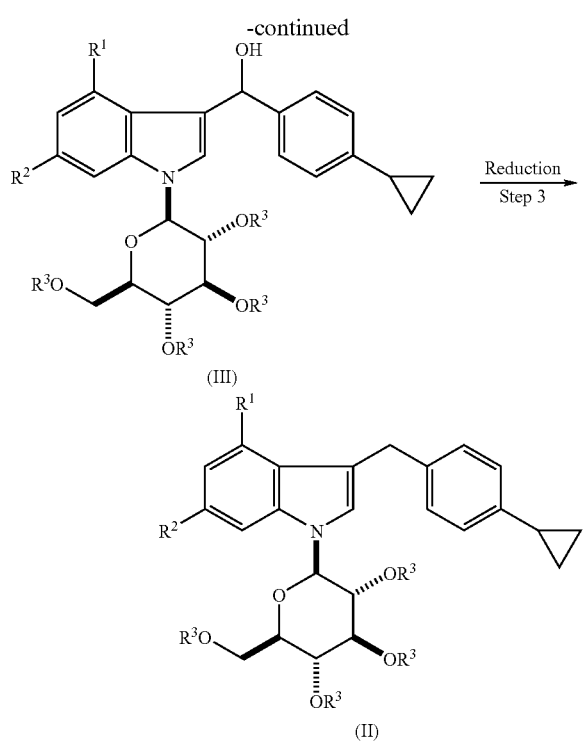

(In the above scheme, the symbols are the same as defined above.)

Step 1:

The compounds of formula (IV) can be prepared by formylation of the compounds of formula (V) with a Vilsmeier reagent or α,α-dichloromethyl methyl ether/titanium tetrachloride.

The Vilsmeier reagent can be prepared in a conventional manner well known in the art, for example, from dimethylformamide or N-methylformanilide/phosphorus oxychloride, thionyl chloride or oxalyl chloride.

The reaction is typically carried out in a suitable solvent such as dimethylformamide or dichloroethane at ambient or elevated temperature, for example, from 25° C. to 80° C.

Step 2:

The compounds of formula (III) can be prepared by coupling the compounds, of formula (IV) with ArLi, ArMgBr, ArZnBr, Ar(Me)$_2$LiZn or ArB(OH)$_2$, wherein Ar is the following formula:

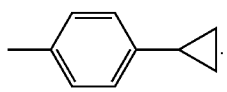

The coupling reaction of the compounds (1V) with ArLi, ArMgBr, ArZnBr or Ar(Me)$_2$LiZn can be typically carried out in a suitable solvent being an inert organic solvent such as diethyl ether, tetrahydrofuran, or 1,4-dioxane at ambient or lowered temperature, for example, −78° C. to 25° C.

The coupling reaction of the compounds (IV) with ArB(OH)$_2$ can be typically carried out in the presence of a catalyst such as (acetylacetonato)dicarbonylrhodium (I) or hydroxyl-(1,5-cyclooctadiene)rhodium(I) dimer and a ligand such as 1,1'-bis(diphenylphosphino)ferrocene or tri-tert-butyl-phosphine in a suitable solvent being an inert solvent such as tetrahydrofuran, dimethoxyethane and 1,4-dioxane at ambient or elevated temperature, for example, 25° C. to 100° C.

Step 3:

The compounds of formula (II) can be prepared by reducing the compounds of formula (III).

The reduction of the compounds (III) can be carried out by treatment with a silane reagent or a borohydride in the presence of an acid in a suitable solvent or without a solvent.

Examples of the acid include a Lewis acid such as boron trifluoride•diethyl ether complex and titanium tetrachloride, and a strong organic acid such as trifluoroacetic acid, and methanesulfonic acid.

Examples of silane reagents include trialkylsilanes such as triethylsilane, triisopropylsilane.

Examples of borohydrides include sodium borohydride and sodium triacetoxyborohydride.

The solvent can be selected from anyone which does not disturb the reaction, and examples of the solvent include acetonitrile, halogeno alkanes (e.g., dichloromethane, chloroform and dichloroethane), and a mixture of these solvents.

The reduction can be carried out at lowered or ambient temperature, for example, from −30° C. to 25° C.

Scheme 2:

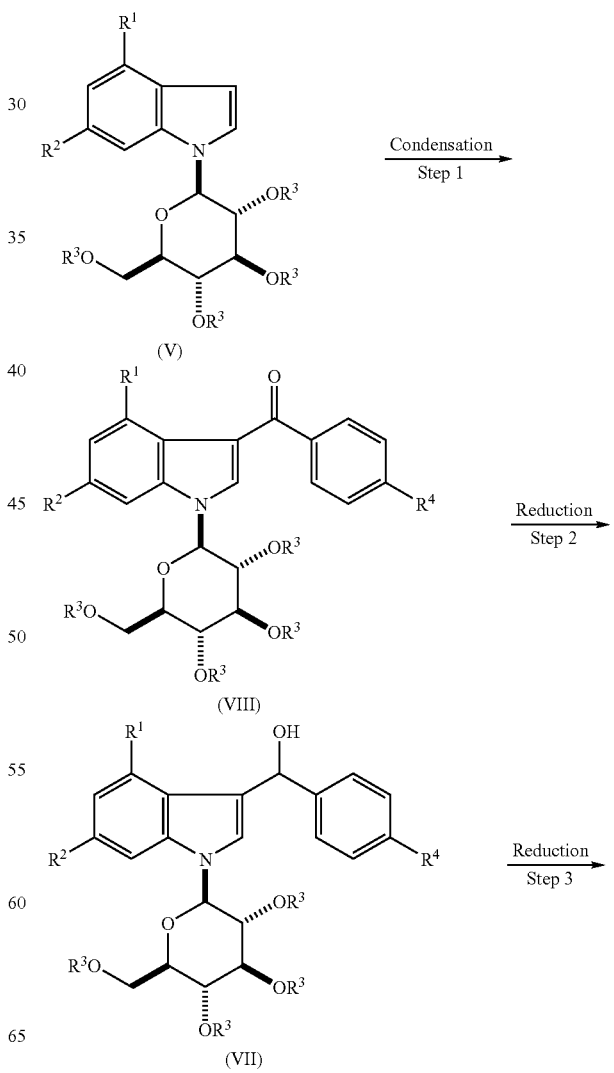

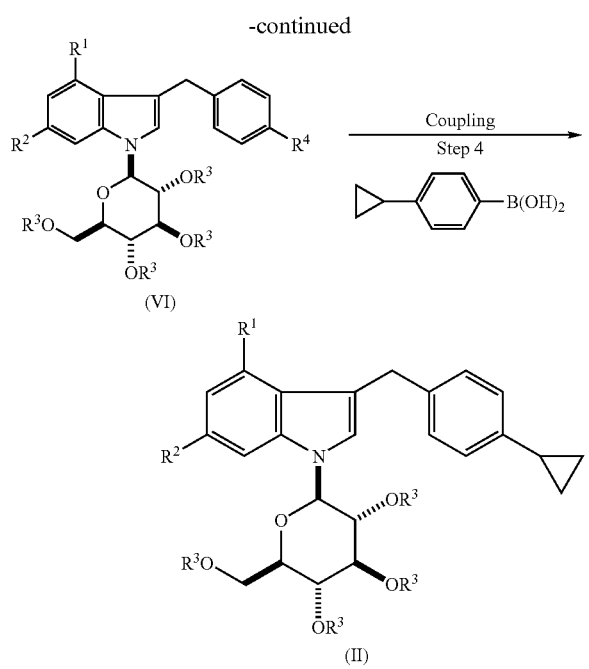

(In the above scheme, $R^4$ is bromine, or iodine, and the other symbols are the same as defined above.)

Step 1:

The compounds of formula (VIII) can be prepared by condensing the compounds of formula (V) with $R^4$—$C_6H_4$—COCl, wherein $R^4$ is the same as defined above.

The condensation can be carried out, according to the Friedel-Crafts acylation well known in the art, in a suitable solvent in the presence of a Lewis acid.

Examples of the Lewis acid include aluminum chloride, boron trifluoride•diethylether complex, tin(IV) chloride, and titanium tetrachloride.

The solvent can be selected from any one which does not disturb the Friedel-Crafts reaction, and examples of the solvent include halogeno alkanes such as dichloromethane, chloroform, tetrachloromethane and dichloroethane.

The reaction can be carried out at lowered, ambient or elevated temperature, for example, from −30° C. to 60° C.

Step 2:

The compounds of formula (VII) can be prepared by reducing the compounds of formula (VIII).

The reduction can be carried out by treating the compound (VIII) with a reducing agent in a suitable solvent.

Examples of the reducing agent include borohydrides (e.g., sodium borohydride with or without cerium(III) chloride heptahydrate, sodium triacetoxyborohydride) and aluminum hydrides (e.g., lithium aluminum hydride, and diisobutyl aluminum hydride).

The solvent can be selected from anyone which does not disturb the reaction and examples of the solvent include ethers (e.g., tetrahydrofuran, diethyl ether, dimethoxyethane, and dioxane), alcohols (e.g., methanol, ethyl alcohol and 2-propanol) and a mixture of these solvents.

The reduction reaction can be carried out at lowered, or ambient temperature, for example, from −30° C. to 25° C.

Step 3:

The compounds of formula (VI) can be prepared by reducing the compounds of formula (VII).

The reduction of the compounds (VII) can be carried out in accordance with Scheme 1, Step 3.

Step 4:

The compounds of formula (II) can be prepared by coupling the compounds of formula (VI) with cyclopropyl-B(OH)$_2$.

The coupling reaction can be carried out by a conventional aryl coupling method, e.g., Suzuki coupling method (for reference see: Suzuki et al., *Synth. Commun.* 11:513 (1981); Suzuki, *Pure and Appl. Chem.* 57:1749-1758 (1985); Suzuki et al., *Chem. Rev.* 95:2457-2483 (1995); Shieh et al., *J. Org. Chem.* 57:379-381 (1992); Martin et al., *Acta Chemica Scandinavica* 47:221-230 (1993); Wallace et al., *Tetrahedron Lett.* 43:6987-6990 (2002) and Molander et al., *J. Org. Chem.* 68:4302-4314 (2003)).

The coupling reaction can be carried out in the presence of a Pd catalyst and a base with or without a ligand and an additive in a suitable solvent.

Examples of the Pd catalyst are tetrakis(triphenylphosphine)palladium(0), palladium(II) acetate, bis(acetonitrile) dichloropalladium(II), dichlorobis(triphenylphosphine)palladium(II), [1,1'-bis(diphenylphosphino)-ferrocene] dichloropalladium(II) complex with dichloromethane, tris (dibenzylidene-acetone) dipalladium(0)-chloroform adduct and palladium(II) chloride. Examples of the base include alkali metal carbonates (e.g., potassium carbonate, sodium carbonate and sodium bicarbonate), alkali metal phosphates (e.g., potassium phosphate tribasic, sodium phosphate and sodium hydrogen-phosphate), organic bases (e.g., N,N-diisopropylethylamine) and alkali metal fluorides (e.g., cesium fluoride and potassium fluoride). Examples of the ligand include tricyclohexylphosphine and tri(o-tolyl)phosphine. Examples of the additive include copper(I) iodide.

The solvent can be selected from any one which does not disturb the coupling reaction, and examples of the solvent are aromatic hydrocarbons (e.g., benzene, and toluene), ethers (e.g., tetrahydrofuran, 1,2-dimethoxyethane, and 1,4-dioxane), amides (e.g., dimethylformamide, dimethylacetamide, 1,3-dimethyl-2-imidazolidinone and N-methylpyrrolidone), alcohols (methanol, ethyl alcohol, and 2-propanol), water, and a mixture of these solvents.

The coupling reaction can be carried out at ambient or elevated temperature, for example, from 25° C. to 150° C., preferably from 80° C. to 150° C.

The starting compounds of formula (V) can be prepared in accordance with the following scheme:

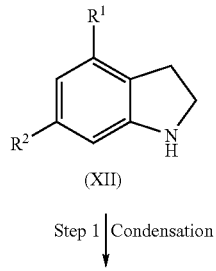

(XII)

Step 1 | Condensation

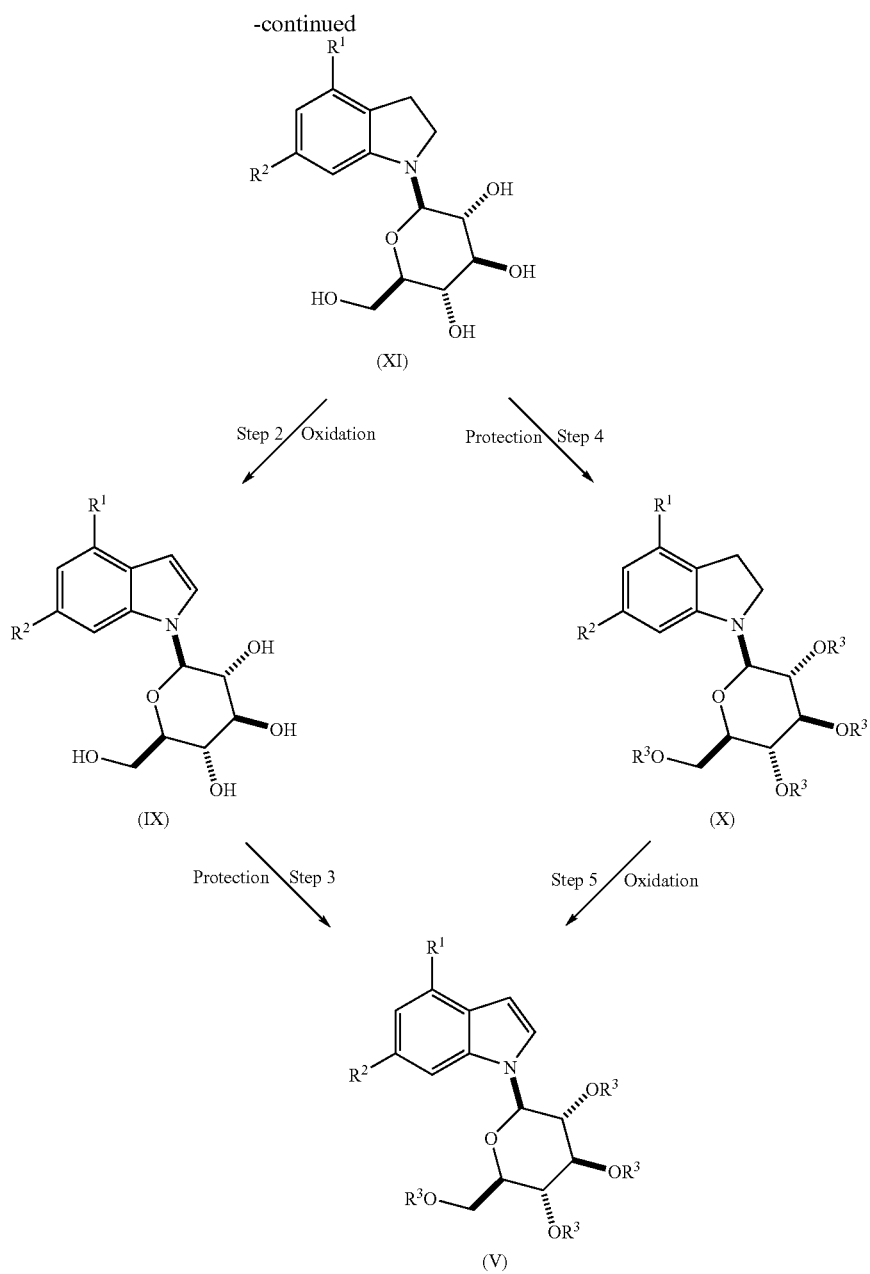

(In the above scheme, the symbols are the same as defined above.)

Step 1:

The compounds of formula (XI) can be prepared by condensing the compounds of formula (XII) with D-glucose. The condensation reaction is typically carried out in a suitable solvent such as acetonitrile, water and alcohols (e.g., methanol, ethyl alcohol and 1-propanol) with or without catalysts such as ammonium chloride and acetic acid at ambient or elevated temperature.

Step 2:

The compounds of formula (IX) can be prepared by oxidation of the compounds of formula (XI). The oxidation reaction can be typically carried out in the presence of a oxidizing reagent such as palladium on charcoal, tetrachloro-1,4-benzoquinone (chloranil), 2,3-dichloro-5,6-dicyano-1,4-benzoquinone (DDQ) or ethylenebis(salicylimine)cobalt(II) salt in a suitable solvent such as ethers (e.g., diethyl ether, tetrahydrofuran, and 1,4-dioxane), halogenoalkanes (e.g., dichloromethane, chloroform, and 1,2-dichloroethane), water and a mixture of these solvents at ambient or lowered temperature.

Step 3:

The compounds of formula (V) can be prepared by protecting hydroxy groups of the compounds of formula (IX). The protecting group for the hydroxy groups can be selected from those conventionally used as protecting groups for a hydroxy group. Examples of the protecting group for a hydroxy group include alkanoyl group (e.g., acetyl), arylalkyl group (e.g., benzyl, tolyl, and anisyl), alkylsilyl group (e.g., trimethylsilyl, t-butyldimethylsilyl, and triethylsilyl). The protection can be carried out by conventional methods well known to those skilled in the art. For a general description of protecting groups and their use, see T. W. Greene et al., "Protecting Groups in Organic Synthesis", John Wiley & Sons, New York, 1999.

Step 4:

The compounds of formula (X) can be prepared by protecting hydroxy groups of the compounds of formula (XI) in accordance with Step 3.

Step 5:

The compounds of formula (V) can be also prepared by oxidation of the compounds of formula (X) in accordance with Step 2.

The compounds of formula (XII) can be prepared in accordance with the following scheme:

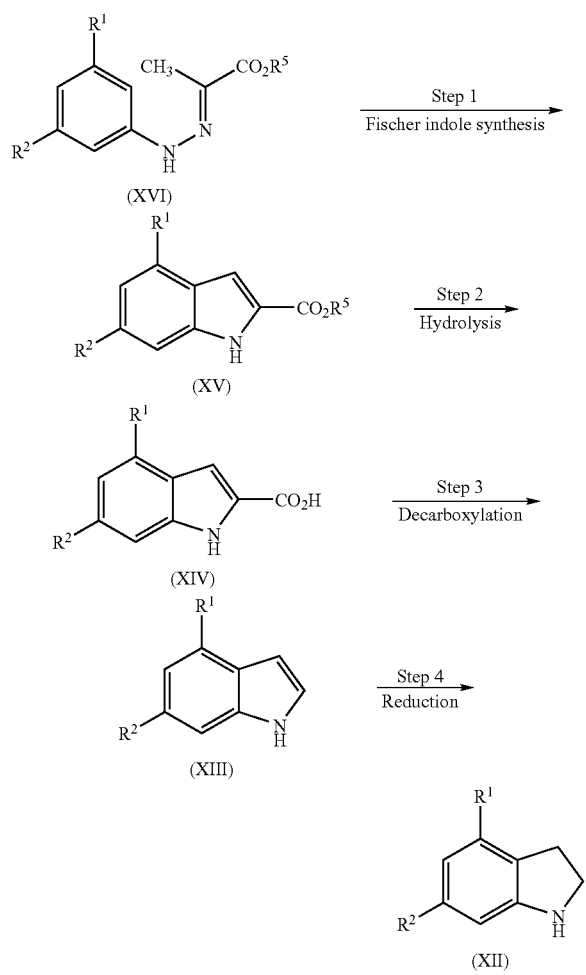

(In the above scheme, $R^5$ is alkyl, and the other symbols are the same as defined above.)

Step 1:

The compounds of formula (XV) can be prepared by cyclizing the compounds of formula (XVI). The cyclization reaction can be carried out according to Fischer indole synthesis well known in the art (cf.: Chem. Rev., 63, 373, 1963). This reaction is typically carried out in a suitable solvent such as alcohols (e.g., methanol and ethyl alcohol) and hydrocarbons (e.g., toluene, nitrobenzene) or without solvent with an acid such as Lewis acid (e.g., zinc chloride), inorganic acid (e.g., hydrochloric acid and polyphosphoric acid) and organic acid (e.g., acetic acid and trifluoroacetic acid) at elevated temperature.

Step 2:

The compounds of formula (XIV) can be prepared by hydrolyzing the compounds of formula (XV). The hydrolysis reaction can be typically carried out in a suitable solvent such as water, alcohols (e.g., methanol and ethyl alcohol) and ethers (e.g., dioxane and tetrahydrofuran) with a base such as alkali metal hydroxides (e.g., lithium hydroxide, potassium hydroxide and sodium hydroxide) at lowered, ambient or elevated temperature.

Step 3:

The compounds of formula (XIII) can be prepared by decarboxylation of the compounds of formula (XIV). The decarboxylation can be typically carried out in a suitable solvent such as quinoline with a catalyst such as copper at elevated temperature.

Step 4:

The compounds of formula (XII) can be prepared by reducing the compounds of formula (XIII). The reduction reaction can be typically carried out in a suitable solvent such as acetonitrile, halogenoalkanes (e.g., dichloromethane and dichloroethane) and ethers (e.g., diethyl ether, tetrahydrofuran and dioxane) with a reducing agent such as triethylsilane, zinc borohydride, borane-trimethylamine complex, borane-morpholine complex and sodium cyanoborohydride in the presence of an acid include a Lewis acid such as trifluoroacetic acid, boron trifluoride•diethyl ether complex, hydrochloric acid and acetic acid at ambient or elevated temperature.

The compounds of formula (XVI) can be prepared by condensing compounds of formula (XVII):

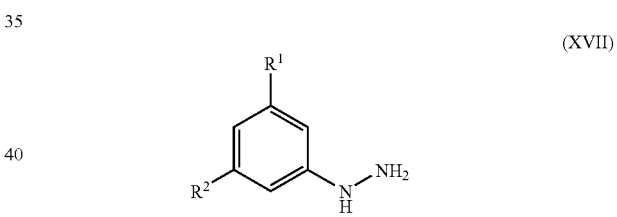

wherein the symbols are the same as defined above, with $CH_3COCO_2R^5$ wherein $R^5$ is as defined above. The condensation reaction can be typically carried out in a suitable solvent such as acetonitrile, halogenoalkanes (e.g., dichloromethane and chloroform) and ethers (e.g., dioxane), water and alcohols (e.g., methanol, ethyl alcohol and 1-propanol) with or without a base (e.g., sodium acetate and potassium acetate) or an acid (e.g., hydrochloric acid and acetic acid) at ambient or elevated temperature.

Alternatively, the compounds of formula (XVI) can be prepared by (1) reacting the compounds of formula (XVIII):

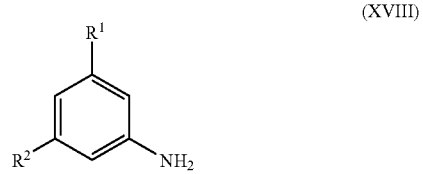

wherein the symbols are as defined above, with sodium nitrite in the presence of an acid such as hydrochloric acid in a suitable solvent such as water and alcohols (e.g., methanol and ethyl alcohol) at ambient or lowered temperature, to give a corresponding aryldiazonium salt, and (2) condensing the aryldiazonium salt with $CH_3COCH(CH_3)CO_2R^5$ wherein $R^5$ is as defined above, in the presence of a base such as sodium acetate, potassium hydroxide in a suitable solvent such as water and alcohols (e.g., methanol and ethyl alcohol) at lowered or ambient temperature.

The other starting compounds are commercially available or may be easily prepared by conventional methods well known to those skilled in the art.

Hereinafter, the present invention will be illustrated by Examples and Reference Examples, but the present invention should not be construed to be limited thereto.

EXAMPLES

Example 1

3-(4-Cyclopropylphenylmethyl)-4-fluoro-1-(β-D-gluco-pyranosyl)indole

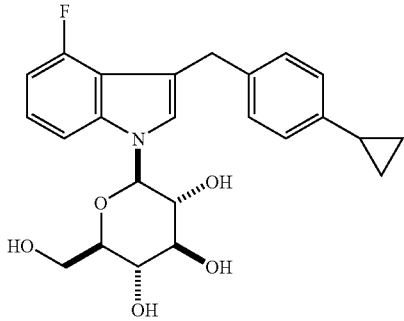

(1) A mixture of 4-fluoroindoline (185 mg) and D-glucose (267 mg) in $H_2O$ (0.74 ml)-ethyl alcohol (9 ml) was refluxed under argon atmosphere for 24 hours. The solvent was evaporated under reduced pressure to give crude 4-fluoro-1-(β-D-glucopyranosyl)indoline, which was used in the subsequent step without further purification.

(2) The above compound was suspended in chloroform (8 ml), and thereto were added successively pyridine (0.873 ml), acetic anhydride (1.02 ml) and 4-(dimethylamino)pyridine (a catalytic amount). After being stirred at room temperature for 21 hours, the reaction solvent was evaporated under reduced pressure. The residue was dissolved in ethyl acetate, and the solution was washed with a 10% aqueous copper (II) sulfate solution twice and a saturated aqueous sodium hydrogen carbonate solution, and dried over magnesium sulfate. The insoluble materials were filtered off, and the filtrate was evaporated under reduced pressure. The residue was purified by silica gel column chromatography (hexane:ethyl acetate=90:10-60:40) to give 4-fluoro-1-(2,3,4,6-tetra-O-acetyl-β-D-glucopyranosyl)indoline (365 mg) as colorless amorphous. APCI-Mass m/Z 468 (M+H). $^1$H-NMR (DMSO-$d_6$) δ 1.93 (s, 3H), 1.96 (s, 3H), 1.97 (s, 3H), 2.00 (s, 3H), 2.83 (ddd, J=15.5, 10.5 and 10.3 Hz, 1H), 2.99-3.05 (m, 1H), 3.49-3.57 (m, 2H), 3.95-3.99 (m, 1H), 4.07-4.11 (m, 2H), 4.95 (t, J=9.5 Hz, 1H), 5.15 (t, J=9.4 Hz, 1H), 5.42 (t, J=9.6 Hz, 1H), 5.49 (d, J=9.3 Hz, 1H), 6.48 (t, J=8.6 Hz, 1H), 6.60 (d, J=8.0 Hz, 1H), 7.05-7.10 (m, 1H).

(3) The above compound (348 mg) was dissolved in 1,4-dioxane (14 ml), and thereto was added 2,3-dichloro-5,6-dicyano-1,4-benzoquinone (306 mg). After being stirred at room temperature for 33 hours, thereto was added a saturated aqueous sodium hydrogen carbonate solution (20 ml), and the organic solvent was evaporated under reduced pressure. The residue was extracted with ethyl acetate twice, and the combined organic layer was washed with brine, dried over magnesium sulfate and treated with activated carbon. The insoluble materials were filtered off, and the filtrate was evaporated under reduced pressure. The residue was purified by silica gel column chromatography (hexane:ethyl acetate=90:10-60:40) and recrystallization from ethyl alcohol to give 4-fluoro-1-(2,3,4,6-tetra-O-acetyl-β-D-glucopyranosyl)indole (313 mg) as colorless crystals. mp 132-135° C. APCI-Mass m/Z 483 (M+$NH_4$). $^1$H-NMR (DMSO-$d_6$) δ 1.64 (s, 3H), 1.97 (s, 3H), 1.99 (s, 3H), 2.04 (s, 3H), 4.10 (ABX, J=12.4, 2.7 Hz, 1H), 4.14 (ABX, J=12.4, 5.2 Hz, 1H), 4.31 (ddd, J=10.0, 5.2 and 2.7 Hz, 1H), 5.25 (t, J=9.7 Hz, 1H), 5.53 (t, J=9.5 Hz, 1H), 5.61 (t, J=9.3 Hz, 1H), 6.22 (d, J=9.0 Hz, 1H), 6.58 (d, J=3.4 Hz, 1H), 6.88 (dd, J=10.8, 7.9 Hz, 1H), 7.19 (td, J=8.1, 5.3 Hz, 1H), 7.51 (d, J=8.5 Hz, 1H), 7.53 (d, J=3.4 Hz, 1H).

(4) The above compound (3.50 g) and N,N-dimethylformamide (3.49 ml) were dissolved in 1,2-dichloroethane (70 ml), and thereto was added dropwise phosphorus (III) oxychloride (2.10 ml). The mixture was stirred at 70° C. for 1 hour, and thereto was added water (100 ml) at 0° C. The resultant mixture was extracted with ethyl acetate (200 ml) twice, and the combined organic layer was washed with brine (40 ml) and dried over magnesium sulfate. The insoluble materials were filtered off, and the filtrate was evaporated under reduced pressure. The residue was purified by silica gel column chromatography (hexane:ethyl acetate=90:10-50:50) and recrystallization from ethyl alcohol (20 ml) to give 4-fluoro-1-(2,3,4,6-tetra-O-acetyl-β-D-glucopyranosyl)-indole-3-carboxaldehyde (2.93 g) as colorless crystals. mp 190-192° C. APCI-Mass m/Z 511 (M+$NH_4$). $^1$H-NMR (DMSO-$d_6$) δ 1.64 (s, 3H), 1.98 (s, 3H), 2.00 (s, 3H), 2.05 (s, 3H), 4.12 (A part of ABX, J=12.4, 2.5 Hz, 1H), 4.17 (B part of ABX, J=12.4, 5.5 Hz, 1H), 4.33 (ddd, J=10.0, 5.5 and 2.5 Hz, 1H), 5.32 (t, J=9.8 Hz, 1H), 5.56 (t, J=9.6 Hz, 1H), 5.66 (t, J=9.3 Hz, 1H), 6.36 (d, J=9.0 Hz, 1H), 7.11 (dd, J=10.6, 8.0 Hz, 1H), 7.38 (td, J=8.1, 5.1 Hz, 1H), 7.65 (d, J=8.3 Hz, 1H), 8.53 (s, 1H), 10.0 (d, J=2.9 Hz, 1H).

(5) To a mixture of magnesium turnings (664 mg) and 1,2-dibromoethane (one drop) in tetrahydrofuran (40 ml) was added dropwise a solution of 1-bromo-4-cyclopropylbenzene (see WO 96/07657) (5.21 g) in tetrahydrofuran (12 ml) over 25 minutes under being stirred vigorously, and the mixture was vigorously stirred for 30 minutes at room temperature. The resultant mixture was then dropwise added to a solution of the above 4-fluoro-1-(2,3,4,6-tetra-O-acetyl-β-D-glucopyranosyl)indole-3-carboxaldehyde (4.35 g) in tetrahydrofuran (130 ml) over 15 minutes at −78° C. under argon atmosphere. The mixture was stirred at same temperature for 30 minutes, and thereto was added a saturated aqueous ammonium chloride solution (200 ml). The resultant mixture was extracted with ethyl acetate (150 ml) twice, and the combined organic layer was dried over magnesium sulfate. The insoluble materials were filtered off, and the filtrate was evaporated under reduced pressure to give crude 4-cyclopropylphenyl 4-fluoro-1-(2,3,4,6-tetra-O-acetyl-β-D-glucopyranosyl)indol-3-yl methanol, which was used in the subsequent step without further purification.

(6) To a stirred solution of the above compound and triethylsilane (2.11 ml) in dichloromethane (44 ml)—acetonitrile (87 ml) was added boron trifluoride•diethyl ether complex (1.34 ml) at 0° C. under argon atmosphere. The mixture was stirred at same temperature for 20 minutes, and thereto was added a saturated aqueous sodium hydrogen carbonate solution (200 ml). The organic solvent was evaporated under reduced pressure, and the residue was extracted with ethyl acetate (150 ml) twice. After being dried over magnesium sulfate, the insoluble materials were filtered off, and the filtrate was evaporated under reduced pressure. The residue was purified by silica gel column chromatography (hexane:ethyl acetate=90:10-50:50) and trituration with ethyl alcohol (40 ml) to give 3-(4-cyclopropylphenylmethyl)-4-fluoro-1-(2,3,4,6-tetra-O-acetyl-β-D-glucopyranosyl)indole (4.71 g) as colorless crystals. mp 190-192° C. APCI-Mass m/Z613 (M+NH$_4$). $^1$H-NMR (DMSO-d$_6$) δ 0.60 (ddd, J=6.6, 4.7 and 4.3 Hz, 2H), 0.88 (ddd, J=8.3, 6.3 and 4.0 Hz, 2H), 1.63 (s, 3H), 1.81-1.87 (m, 1H), 1.96 (s, 3H), 1.99 (s, 3H), 2.04 (s, 3H), 4.00 (s, 2H), 4.09 (A part of ABX, J=12.2, 2.4 Hz, 1H), 4.13 (B part of ABX, J=12.3, 5.5 Hz, 1H), 4.28 (ddd, J=10.0, 5.3 and 2.7 Hz, 1H), 5.23 (t, J=9.6 Hz, 1H), 5.49-5.56 (m, 2H), 6.15 (d, J=8.7 Hz, 1H), 6.77 (dd, J=11.0, 7.9 Hz, 1H), 6.95 (d, J=8.2 Hz, 2H), 7.05 (d, J=8.0 Hz, 2H), 7.14 (td, J=8.0, 5.1 Hz, 1H), 7.23 (s, 1H), 7.46 (d, J=8.3 Hz, 1H).

(7) The above compound (4.67 g) was dissolved in methanol (47 ml)—tetrahydrofuran (93 ml), and thereto was added sodium methoxide (28% methanol solution, 1 drop). After being stirred at room temperature for 1 hour, the reaction solvent was evaporated under reduced pressure. The residue was purified by silica gel column chromatography (chloroform:methanol=99:1-90:10) to give the titled compound, 3-(4-cyclopropylphenylmethyl)-4-fluoro-1-(β-D-glucopyranosyl)indole (3.23 g) as colorless foam. This foam was crystallized from ethyl alcohol—H$_2$O to give hemihydrate of the titled compound as colorless crystals. mp 110-112° C. APCI-Mass m/Z 445 (M+NH$_4$), 428 (M+H). $^1$H-NMR (DMSO-d$_6$) δ 0.60 (m, 2H), 0.88 (ddd, J=8.3, 6.3 and 4.1 Hz, 2H), 1.82-1.87 (m, 1H), 3.23 (td, J=9.0, 5.4 Hz, 1H), 3.39 (td, J=8.9, 5.1 Hz, 1H), 3.42-3.46 (m, 2H), 3.63-3.68 (m, 2H), 4.02 (s, 2H), 4.53 (t, J=5.6 Hz, 1H), 5.10 (d, J=5.3 Hz, 1H), 5.17 (d, J=5.0 Hz, 1H), 5.21 (d, J=5.9 Hz, 1H), 5.37 (d, J=9.2 Hz, 1H), 6.74 (dd, J=11.1, 7.9 Hz, 1H), 6.96 (d, J=8.2 Hz, 2H), 7.07 (td, J=8.1, 5.2 Hz, 1H), 7.13 (d, J=8.2 Hz, 2H), 7.21 (s, 1H), 7.35 (d, J=8.3 Hz, 1H). Anal. Calcd. for C$_{24}$H$_{26}$FNO$_5$.0.5H$_2$O: C, 66.04; H, 6.23; F, 4.35; N, 3.21. Found: C, 65.62; H, 6.27; F, 4.32; N, 3.11.

Example 2

4-Chloro-3-(4-cyclopropylphenyl-methyl)-1-(β-D-glucopyranosyl)indole

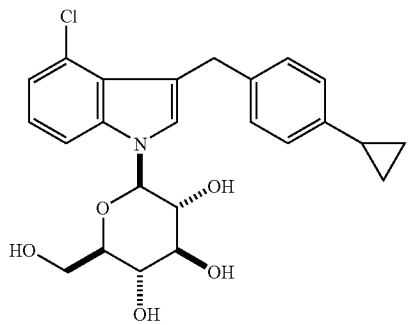

(1) A mixture of 4-chloroindoline (2.88 g) and D-glucose (3.38 g) in ethyl alcohol (150 ml)-H$_2$O (10 ml) was refluxed under argon atmosphere overnight. The solvent was evaporated under reduced pressure and the residue was purified by silica gel column chromatography (chloroform:methanol=100:0-88:12) to give 4-chloro-1-(β-D-glucopyranosyl)indoline (3.35 g) as a colorless foam. APCI-Mass m/Z 316/318 (M+H). $^1$H-NMR (DMSO-d$_6$) δ 2.87-3.02 (m, 2H), 3.07-3.12 (m, 1H), 3.20-3.32 (m, 2H), 3.38-3.47 (m, 2H), 3.51-3.60 (m, 2H), 3.68-3.73 (m, 1H), 4.34-4.37 (m, 1H), 4.63 (d, J=8.3-Hz, 1H), 4.93 (d, J=5.1 Hz, 1H), 5.03 (d, J=4.0 Hz, 1H), 5.06 (d, J=4.5 Hz, 1H), 6.53 (d, J=8.0 Hz, 1H), 6.60 (d, J=8.0 Hz, 1H), 6.99 (t, J=7.9 Hz, 1H).

(2) The above compound (3.3 g) was dissolved in 1,4-dioxane (150 ml), and thereto was added 2,3-dichloro-5,6-dicyano-1,4-benzoquinone (2.85 g). The mixture was stirred at room temperature for 12 hours. To the reaction mixture was added a saturated aqueous sodium hydrogen carbonate solution (300 ml), and the mixture was extracted with ethyl acetate 3 times. The combined organic layer was washed with a saturated aqueous sodium hydrogen carbonate solution and dried over magnesium sulfate. The insoluble materials were filtered off, and the filtrate was evaporated under reduced pressure. The residue was purified by silica gel column chromatography (chloroform:methanol=100:0-86:14) to give 4-chloro-1-(β-D-glucopyranosyl)indole (2.01 g) as pale brown crystals. APCI-Mass m/Z 314/316 (M+H). $^1$H-NMR (DMSO-d$_6$) δ 3.24-3.50 (m, 4H), 3.68-3.74 (m, 2H), 4.54 (t, J=5.5 Hz, 1H), 5.11 (d, J=5.3 Hz, 1H), 5.20 (d, J=4.8 Hz, 1H), 5.28 (d, J=5.8 Hz, 1H), 5.44 (d, J=9.2 Hz, 1H), 6.51 (d, J=3.4 Hz, 1H), 7.11-7.16 (m, 2H), 7.57-7.58 (m, 2H).

(3) The above compound (2.01 g) was suspended in dichloromethane (100 ml), and thereto were added successively acetic anhydride (4.24 ml), N,N-diisopropylethylamine (7.8 ml) and 4-(dimethylamino)pyridine (78 mg). After being stirred at room temperature for 30 minutes, the mixture was washed successively with an aqueous citric acid solution, water and a saturated aqueous sodium hydrogen carbonate solution. The organic layer was dried over magnesium sulfate. The insoluble materials were filtered off, and the filtrate was evaporated under reduced pressure. The residue was purified by crystallization from diethyl ether—hexane to give 4-chloro-1-(2,3,4,6-tetra-O-acetyl-β-D-glucopyranosyl)-indole (2.94 g) as colorless crystals. APCI-Mass m/Z499/501 (M+NH$_4$) $^1$H-NMR (DMSO-d$_6$) δ 1.65 (s, 3H), 1.97 (s, 3H), 1.99 (s, 3H), 2.04 (s, 3H), 4.08-4.16 (m, 2H), 4.28-4.32 (m, 1H), 5.26 (t, J=9.8 Hz, 1H), 5.53 (t, J=9.5 Hz, 1H), 5.62 (t, J=9.3 Hz, 1H), 6.23 (d, J=9.2 Hz, 1H), 6.56 (d, J=3.4 Hz, 1H), 7.16 (d, J=8.2 Hz, 1H), 7.21 (t, J=7.9 Hz, 1H), 7.61 (d, J=3.5 Hz, 1H), 7.67 (d, J=8.2 Hz, 1H).

(4) The above compound was treated in a manner similar to Example 1-(4) to give 4-chloro-1-(2,3,4,6-tetra-O-acetyl-β-D-gluco-pyranosyl)indole-3-carboxaldehyde as a colorless powder. APCI-Mass m/Z 527/529 (M+NH$_4$). $^1$H-NMR (DMSO-d$_6$) δ 1.64 (s, 3H) 1.98 (s, 3H), 1.99 (s, 3H), 2.05 (s, 3H), 4.09-4.19 (m, 2H), 4.30 (m, 1H), 5.34 (t, J=9.8 Hz, 1H), 5.54 (t, J=9.5 Hz, 1H), 5.70 (t, J=9.3 Hz, 1H), 6.37 (d, J=9.0 Hz, 1H), 7.35-7.42 (m, 2H), 7.82 (d, J=7.5 Hz, 1H), 8.54 (s, 1H), 10.51 (s, 1H).

(5) The above compound and 1-bromo-4-cyclopropylbenzene (see WO 96/07657) were treated in a manner similar to Example 1-(5) to give crude 4-chloro-1-(2,3,4,6-tetra-O-acetyl-β-D-gluco-pyranosyl)indol-3-yl 4-cyclopropylphenyl methanol, which was used in the subsequent step without further purification.

(6) The above compound was treated in a manner similar to Example 1-(6) to give 4-chloro-3-(4-cyclopropylphenylmethyl)-1-(2,3,4,6-tetra-O-acetyl-β-D-glucopyranosyl)indole as a colorless solid. APCI-Mass m/Z 629/631 (M+NH$_4$). $^1$H-NMR (DMSO-d$_6$) δ 0.58-0.62 (m, 2H), 0.88-0.92 (m, 2H), 1.65 (s, 3H), 1.82-1.88 (m, 1H), 1.96 (s, 3H), 1.99 (s, 3H), 2.03 (s, 3H), 4.07-4.13 (m, 2H), 4.15 (ABq, J=16.2 Hz, 1H), 4.19 (ABq, J=16.2 Hz, 1H), 4.28 (m, 1H), 5.24 (t, J=9.6 Hz, 1H), 5.50 (t, J=9.3 Hz, 5.55 (t, J=9.2 Hz, 1H), 6.17 (d, J=8.7 Hz, 1H), 6.95 (d, J=8.0 Hz, 2H), 7.02 (d, J=8.0 Hz, 2H), 7.05 (d, J=7.7 Hz, 1H), 7.16 (t, J=7.9 Hz, 1H), 7.25 (s, 1H), 7.64 (d, J=8.3 Hz, 1H).

(7) The above compound was treated in a manner similar to Example 1-(7) to give the titled compound, 4-chloro-3-(4-cyclopropyl-phenylmethyl)-1-(β-D-glucopyranosyl) indole as a colorless powder. APCI-Mass m/Z 444/446 (M+H), 461/463 (M+NH$_4$). $^1$H-NMR (DMSO-d$_6$) δ 0.59-0.62 (m, 2H), 0.87-0.92 (m, 2H), 1.82-1.89 (m, 1H), 3.20-3.48 (m, 4H), 3.60-3.70 (m, 2H), 4.21 (s, 2H), 4.54 (t, J=5.5 Hz, 1H), 5.10 (d, J=5.3 Hz, 1H), 5.17 (d, J=5.1 Hz, 1H), 5.21 (d, J=5.9 Hz, 1H), 5.39 (d, J=9.0 Hz, 1H), 6.96 (d, J=8.2 Hz, 2H), 7.02 (d, J=7.2 Hz, 1H), 7.09 (d, J=8.0 Hz, 2H), 7.09 (t, J=7.8 Hz, 1H), 7.22 (s, 1H), 7.53 (d, J=8.2 Hz, 1H).

Example 3

3-(4-Cyclopropylphenylmethyl)-4,6-difluoro-1-(β-D-gluco-pyranosyl) indole

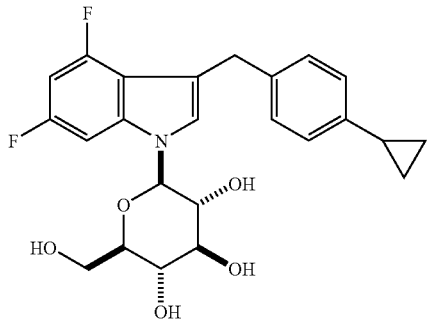

The titled compound was obtained as colorless foam in a manner similar to Example 1 from 4,6-difluoroindoline. APCI-Mass m/Z 463 (M+NH$_4$). $^1$H-NMR (DMSO-d$_6$) δ 0.58-0.62 (m, 2H), 0.88-0.91 (m, 2H), 1.82-1.88 (m, 1H), 3.20-3.50 (m, 4H), 3.59-3.70 (m, 2H), 3.99 (s, 2H), 4.54 (t, J=5.7 Hz, 1H), 5.10 (d, J=5.3 Hz, 1H), 5.19 (d, J=5.0 Hz, 1H), 5.22 (d, J=5.8 Hz, 1H), 5.35 (d, J=9.0 Hz, 1H), 6.78 (t, J=9.6 Hz, 1H), 6.96 (d, J=8.0 Hz, 2H), 7.11 (d, J=8.0 Hz, 2H), 7.22 (s, 1H), 7.30 (dd, J=10.0, 1.7 Hz, 1H).

Example 4

4-Chloro-3-(4-cyclopropylphenylmethyl)-6-fluoro-1-(β-D-gluco-pyranosyl) indole

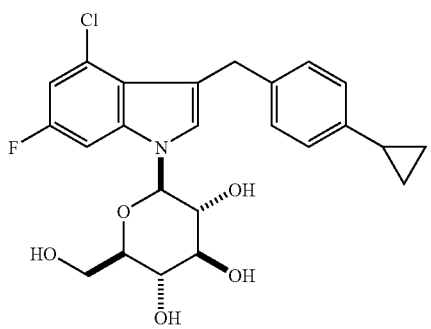

The titled compound was obtained as colorless foam in a manner similar to Example 1 from 4-chloro-6-fluoroindoline. APCI-Mass m/Z 479/481 (M+NH$_4$). $^1$H-NMR (DMSO-d$_6$) δ 0.59-0.62 (m, 2H), 0.88-0.91 (m, 2H), 1.83-1.87 (m, 1H), 3.21-3.50 (m, 4H), 3.57-3.63 (m, 1H), 3.65-3.71 (m, 1H), 4.18 (s, 2H), 4.54 (t, J=5.5 Hz, 1H), 5.10 (d, J=5.3 Hz, 1H), 5.16 (d, J=5.0 Hz, 1H), 5.23 (d, J=5.8 Hz, 1H), 5.38 (d, J=9.0 Hz, 1H), 6.97 (d, J=8.2 Hz, 2H), 7.01 (dd, J=9.4, 2.0 Hz, 1H), 7.08 (d, J=8.0 Hz, 2H), 7.22 (s, 1H), 7.47 (dd, J=10.1, 2.1 Hz, 1H).

Reference Example 1

4-Fluoroindoline

To a stirred suspension of sodium borohydride (560 mg) in diethylether (6 ml) was added dropwise zinc chloride (1.0M solution in diethyl ether, 7.4 ml). The mixture was stirred at room temperature under argon atmosphere for 1 day. To the resultant mixture was added dropwise a solution of 4-fluoroindole (500 mg) in diethyl ether (5 ml). After being stirred at room temperature under argon atmosphere for 12 days, thereto was added a cold 0.5 N aqueous hydrochloric acid solution (30 ml) at 0° C. After that, the mixture was basified with a cold 2 N aqueous sodium hydroxide solution at 0° C., and extracted with ethyl acetate 3 times. The combined organic layer was dried over magnesium sulfate, and the insoluble materials were filtered off, and the filtrate was evaporated under reduced pressure. The residue was purified by silica gel column chromatography (hexane:ethyl acetate=100:0-80:20) to give the titled compound (351 mg) as pale yellow oil. APCI-Mass m/Z 138 (M+H). $^1$H-NMR (DMSO-d$_6$) δ 2.93 (t, J=8.6 Hz, 2H), 3.46 (t, J=8.6 Hz, 2H), 5.78 (br-s, 1H), 6.24-6.31 (m, 2H), 6.87-6.94 (m, 1H).

Reference Example 2

4-Chloroindoline

A solution of 4-chloroindole (3.15 g) and triethylsilane (8.30 ml) in trifluoroacetic acid (32 ml) was stirred at 50° C. for 30 minutes. The solvent was evaporated under reduced pressure, and the residue was basified with a saturated aqueous sodium hydrogen carbonate solution. The mixture was extracted with ethyl acetate twice, and the combined organic layer was dried over magnesium sulfate. The insoluble materials were filtered off, and the filtrate was evaporated under reduced pressure. The residue was purified by silica gel column chromatography (hexane:ethyl acetate=100:0-80:20) to give the titled compound (2.89 g) as colorless oil. APCI-Mass m/Z 154/156 (M+H). $^1$H-NMR (DMSO-d$_6$) δ 2.94 (t, J=8.7 Hz, 2H), 3.46 (t, J=8.7 Hz, 2H), 5.83 (s, 1H), 6.40 (d, J=7.7 Hz, 1H), 6.50 (d, J=8.0 Hz, 1H), 6.90 (t, J=7.9 Hz, 1H).

Reference Example 3

4,6-Difluoroindoline (1) A mixture of 3,5-difluorophenyl hydrazine hydrochloride (5.0 g) and ethyl pyruvate (4.6 ml) methyl alcohol (25 ml) was refluxed for 1 hour, and the solvent was evaporated under reduced pressure. The residual solid was triturated with hexane to give ethyl 2-(3,5-difluorophenyl hydrazino)propionate (4.65 g) as colorless crystals. mp 139-141° C. APCI-Mass m/Z 243 (M+H).

(2) A suspension of the above compound (4.65 g) in toluene (47 ml) was added to polyphosphoric acid (23 g), and the mixture was refluxed for 3 hours under argon atmosphere. After being cooled to room temperature, thereto were added water and ethyl acetate, and the resultant mixture was stirred at room temperature. The insoluble materials were filtered off, and the filtrate was separated. The aqueous layer was extracted with ethyl acetate, and the combined organic layer was washed with successively water, a saturated aqueous sodium hydrogen carbonate solution and brine. After being dried over magnesium sulfate and treated with activated carbon, the insoluble materials were filtered off, and the filtrate was evaporated under reduced pressure. The residual solid was triturated with diisopropyl ether—hexane (1:1) to give ethyl 4,6-difluoroindole-2-carboxylate (3.48 g) as pale yellow crystals. mp 153-154° C. ESI-Mass m/Z 224 (M−H).

(3) A mixture of the above compound (3.48 g) in a 4 N aqueous sodium hydroxide solution (7.73 ml) and ethyl alcohol (35 ml) was refluxed for 15 minutes, and the organic solvent was evaporated under reduced pressure. Thereto was added water, and the mixture was washed with ethyl ether followed by being acidified with a 6 N aqueous hydrochloric acid solution. The resultant mixture was extracted with ethyl acetate, and the organic layer was washed with brine, dried over magnesium sulfate and treated with activated carbon. The insoluble materials were filtered off, and the filtrate was evaporated under reduced pressure to give crude 4,6-difluoroindole-2-carboxylic acid (3.01 g) as a pale brown solid. mp 253-254 (dec.). ESI-Mass m/Z 196 (M−H).

(4) A mixture of the above compound (3.0 g) and copper powder (2.9 g) in quinoline (30 ml) was stirred at 200° C. for 5 hours under argon atmosphere. After being cooled to room temperature, the insoluble materials were filtered off and washed with ethyl acetate (100 ml). The filtrate was washed with a 6 N aqueous hydrochloric acid solution twice and brine. The each aqueous layer was extracted with ethyl acetate, and the combined organic layer was dried over magnesium sulfate and treated with activated carbon. The insoluble materials were filtered off, and the filtrate was evaporated under reduced pressure. The residual oil was purified by silica gel column chromatography (hexane:ethyl acetate=10:1-6:1) to give 4,6-difluoroindole (2.60 g) as pale yellow oil. ESI-Mass m/Z 152 (M−H).

(5) The above compound (2.33 g) was dissolved in 1,4-dioxane (30.4 ml), and thereto were added morpholine borane (6.15 g) and a 36% aqueous hydrochloric acid solution (2.64 ml) at room temperature. The mixture was refluxed for 2 hours, and then cooled to room temperature. Thereto was added a 6 N aqueous hydrochloric acid solution (12.2 ml), and the resultant mixture was refluxed for 15 minutes. The mixture was basified with a 10% aqueous sodium hydroxide solution at 0° C., and thereto was added water and extracted with ethyl acetate twice. The combined organic layer was washed with brine and dried over magnesium sulfate. The insoluble materials were filtered off, and the filtrate was evaporated under reduced pressure. The residual oil was purified by silica gel column chromatography (hexane:ethyl acetate=10:1-6:1) to give the titled compound, 4,6-difluoroindoline (2.05 g) as colorless oil. APCI-Mass m/Z 156 (M+H). $^1$H-NMR (DMSO-$d_6$) δ 2.90 (t, J=8.6 Hz, 2H), 3.52 (td, J=7.5, 1.3 Hz, 2H), 6.08-6.14 (m, 2H), 6.17 (td, J=10.0, 2.1 Hz, 1H).

Reference Example 4

4-Chloro-6-fluoroindoline (1) To a suspension of 3-chloro-5-fluoroaniline (8.0 g) in a 6 N aqueous hydrochloric acid solution (28 ml) was added a solution of sodium nitrite (4.17 g) in $H_2O$ (5.2 ml) at 0° C., and the mixture was stirred at 0° C. for 30 minutes. The resultant mixture was added to a solution of potassium hydroxide (17.0 g), sodium acetate (17.0 g) and ethyl 2-methylacetoacetate (8.72 g) in $H_2O$ (80 ml) and ethyl alcohol (64 ml) at 0° C., and the mixture was stirred at the same temperature for 2 hours. The reaction mixture was extracted with ethyl acetate twice, and the combined organic layer was evaporated under reduced pressure. The residue was dissolved in water and ethyl acetate, and the insoluble materials were filtered off. The filtrate was separated, and the organic layer was washed with brine and dried over magnesium sulfate. The insoluble materials were filtered off, and the filtrate was evaporated under reduced pressure. The residual solid was triturated with hexane to give ethyl 2-(3-chloro-5-fluorophenylhydrazino)propionate (4.0 g) as a pale brown solid. APCI-Mass m/Z 259/261 (M+H).

(2) The above compound was treated in a manner similar to Reference Example 3-(2), (3), (4) and (5) to give the titled compound, 4-chloro-6-fluoroindoline as colorless oil. APCI-Mass m/Z172/174 (M+H). $^1$H-NMR (DMSO-$d_6$) δ 2.90 (t, J=9.3 Hz, 2H), 3.52 (t, J=8.7 Hz, 2H), 6.16 (s, 1H), 6.19 (dd, J=10.1, 1.9 Hz, 1H), 6.35 (dd, J=9.5, 1.9 Hz, 1H).

Pharmacological Experiments

1. Assay for SGLT2 Inhibition

Test Compounds:

Compounds described in the above examples were used for the SGLT2 inhibition assay.

Method:

CHOK1 cells expressing human SGLT2 were seeded in 24-well plates at a density of 400,000 cells/well in F-12 nutrient mixture (Ham's F-12) containing 10% fetal bovine serum, 400 μg/ml Geneticin, 50 units/ml sodium penicillin G (Gibco-BRL) and 50 μg/ml streptomycin sulfate. After 2 days of culture at 37° C. in a humidified atmosphere containing 5% $CO_2$, cells were washed once with the assay buffer (137 mM NaCl, 5 mM KCl, 1 mM $CaCl_2$, 1 mM $MgCl_2$, 50 mM Hepes, and 20 mM Tris, pH 7.4) and incubated with 250 μl of the buffer containing test compounds for 10 min at 37° C. Test compounds were dissolved in DMSO. The final concentration of DMSO was 0.5%. The transport reaction was initiated by addition of 50 μl [$^{14}$C]-methyl-α-D-glucopyranoside ($^{14}$C-AMG) solution (final concentration, 0.5 mM). After incubation for 2 hours at 37° C., the uptake was stopped by aspiration of the incubation mixture, the cells were washed three times with ice-cold PBS. Then, cells were solubilized with 0.3 N NaOH and aliquots were taken for determination of radioactivity by a liquid scintillation counter. Nonspecific AMG uptake was defined as that which occurred in the presence of 100 μM of phlorizin, a specific inhibitor of sodium-dependent glucose cotransporter. Specific uptake was normalized for the protein concentrations measured by the method of Bradford. The 50% inhibitory concentration ($IC_{50}$) values were calculated from dose-response curves by least square method.

Results:

Results are shown in the following table:

TABLE 2

| Test Compounds (Example No.) | $IC_{50}$ (nM) |
|---|---|
| 1 | 1.9 |
| 2 | 2.3 |
| 3 | 2.8 |
| 4 | 3.6 |

2. Urinary glucose excretion test in rats

Test compounds:
Compounds described in the above examples were used for the Urinary glucose excretion test in rats.

Methods:
6-week-old male Sprague-Dawley (SD) rats were housed in individual metabolic cages with free access to food and water from 2 days prior to the experiment. On the morning of the experiment, rats were administered vehicle (0.2% carboxymethyl cellulose solution containing 0.2% Tween80) or test compounds (30 mg/kg) by oral gavage at a volume of 10 ml/kg. Then, urine of the rat was collected for 24 hours, and the urine volume was measured. Subsequently, the glucose concentration in urine was quantified using the enzymatic assay kit and the daily amount of glucose excreted in urine per individual was calculated.

Results:
Urinary glucose amounts ranges are depicted by A, B and C. These ranges are as follows: A≧2400 mg; 2400 mg>B≧2000 mg; 2000 mg>C.

TABLE 3

| Test compounds (Example No.) | Urinary glucose |
|---|---|
| 1 | B |
| 2 | A |
| 3 | B |
| 4 | C |

The invention claimed is:

1. A compound of formula (I) or a pharmaceutically acceptable salt thereof:

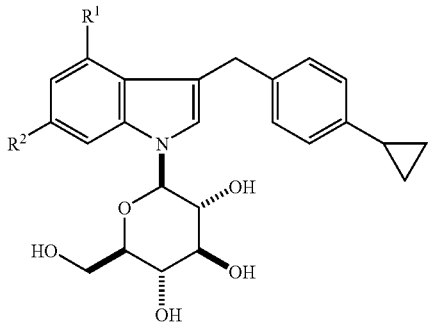

(I)

wherein $R^1$ is fluorine, or chlorine, and $R^2$ is hydrogen, or fluorine.

2. The compound, or a pharmaceutically acceptable salt thereof according to claim 1, wherein $R^1$ is fluorine and $R^2$ is hydrogen, or $R^1$ is chlorine and $R^2$ is hydrogen, or $R^1$ and $R^2$ are both fluorine.

3. The compound, or a pharmaceutically acceptable salt thereof according to claim 1, wherein $R^2$ is hydrogen.

4. The compound according to claim 1, wherein the compound is selected from the group consisting of:
4-chloro-3-(4-cyclopropylphenylmethyl)-1-(β-D-glucopyranosyl)indole,
3-(4-cyclopropylphenylmethyl)-4-fluoro-1-(β3-D-glucopyranosyl)indole,
4-chloro-3-(4-cyclopropylphenylmethyl)-6-fluoro-1-(β-D-glucopyranosyl)indole, and
3-(4-cyclopropylphenylmethyl)-4,6-difluoro-1-(β-D-glucopyranosyl)indole;
or a pharmaceutically acceptable salt thereof.

5. A pharmaceutical composition comprising the compound, or a pharmaceutically acceptable salt thereof as set forth in claim 1 and a pharmaceutically acceptable carrier or diluent.

6. The pharmaceutical composition according to claim 5, which further comprises another antidiabetic agent.

7. A compound, or a pharmaceutically acceptable salt thereof as set forth in claim 1 for use as an active therapeutic substance.

8. A method for treatment or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises
administering to a mammal in need of treatment a therapeutically effective amount of the compound, or a pharmaceutically acceptable salt thereof as set forth in claim 1.

9. A method for treatment of type 1 or type 2 diabetes mellitus, which comprises
administering to a mammal in need of treatment a therapeutically effective amount of the compound, or a pharmaceutically acceptable salt thereof as set forth in claim 1 alone, or in combination with another antidiabetic agent, an agent for treating diabetic complications, an anti-obesity agent, an antihypertensive agent, an antiplatelet agent, an anti-atherosclerotic agent and/or a hypolipidemic agent.

10. A process for preparing a compound of formula:

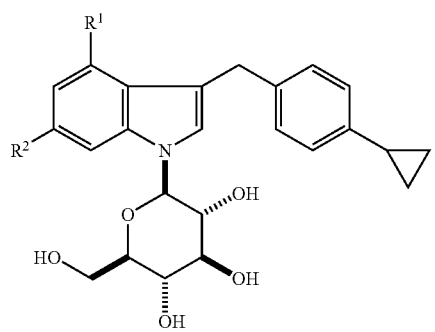

(I)

wherein $R^1$ is fluorine, or chlorine, and $R^2$ is hydrogen, or fluorine, or a pharmaceutically acceptable salt thereof, which comprises deprotecting a compound of formula (II)

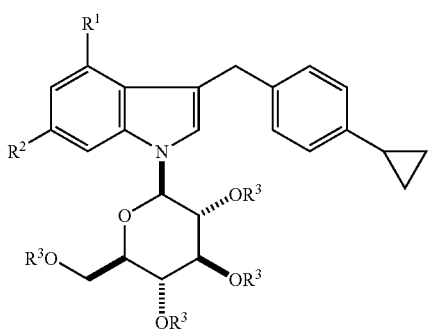

(II)

wherein $R^3$ is a protecting group for hydroxyl group and the other symbols are the same as defined above, followed by converting the resulting compound into a pharmaceutically acceptable salt thereof, if desired.

11. A compound of formula (II)
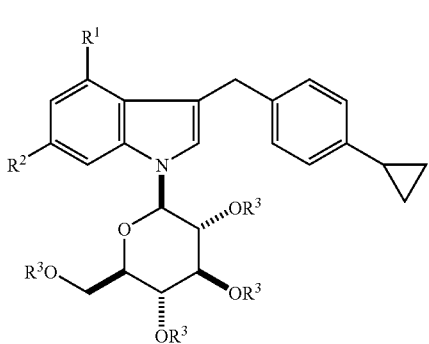
wherein R¹ is fluorine or chlorine, R² is hydrogen or fluorine, and R³ is a protecting group for a hydroxy group, or a pharmaceutically acceptable salt thereof.
12. A compound represented by the formula:
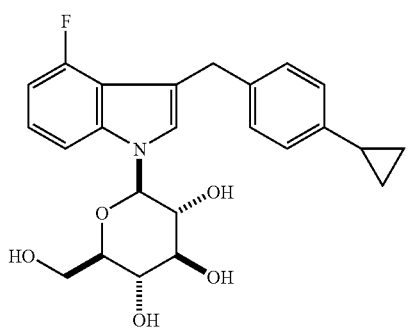
or a pharmaceutically acceptable salt thereof.
* * * * *

UNITED STATES PATENT AND TRADEMARK OFFICE
CERTIFICATE OF CORRECTION

PATENT NO.        : 7,851,617 B2
APPLICATION NO.   : 11/878760
DATED             : December 14, 2010
INVENTOR(S)       : Sumihiro Nomura et al.

It is certified that error appears in the above-identified patent and that said Letters Patent is hereby corrected as shown below:

IN THE CLAIMS:

Claim 4, at column 23, lines 61-62, change:

"3-(4-cyclopropylphenylmethyl)-4-fluoro-1-(β3-D-glucopyranosyl)indole,"

to

-- 3-(4-cyclopropylphenylmethyl)-4-fluoro-1-(β-D-glucopyranosyl)indole, --.

Signed and Sealed this
Ninth Day of August, 2011

David J. Kappos
*Director of the United States Patent and Trademark Office*